United States Patent
Borchert et al.

(10) Patent No.: US 6,472,527 B1
(45) Date of Patent: Oct. 29, 2002

(54) PROCESS FOR THE PREPARATION OF THIAZINE-INDIGO COMPOUNDS AND OF NEW INTERMEDIATES THEREFOR

(75) Inventors: Till Borchert, Saint Louis (FR); Bansi Lal Kaul, Biel-Benken (CH); Bruno Piastra, Huningue; Valérie Wolf, Galfingue, both of (FR)

(73) Assignee: Clariant Finance (BVI) Limited, Tortola (VI)

( * ) Notice: Subject to any disclaimer, the term of this patent is extended or adjusted under 35 U.S.C. 154(b) by 0 days.

(21) Appl. No.: 09/525,839

(22) Filed: Mar. 15, 2000

(30) Foreign Application Priority Data

Mar. 18, 1999 (GB) .............................................. 9906120
Aug. 11, 1999 (GB) .............................................. 9918805

(51) Int. Cl.$^7$ ............................................ C07D 519/00
(52) U.S. Cl. ..................................................... 544/58.4
(58) Field of Search ....................................... 544/58.4

(56) References Cited

U.S. PATENT DOCUMENTS 3,803,139 A * 4/1974 Kaul .......................... 260/243
6,200,378 B1 3/2001 Piastra et al. ................ 106/498

FOREIGN PATENT DOCUMENTS

| DE | 2 151 723 | | 4/1972 |
| DE | 25 36 120 | | 3/1977 |
| DE | 2536120 | * | 3/1977 |
| FR | 1 443 917 | | 12/1966 |
| GB | 1 358 574 | | 7/1974 |
| WO | WO 98/32800 | | 7/1998 |
| WO | 98/32800 | * | 7/1998 |

OTHER PUBLICATIONS

Kaul, B.L., Helv Chim. Acta, 57, 1974, 2664–2678.*
Teitei, T., Aust. J. Chem., 39, 1986, 503–510.*
Gupta, R.R. et al, Heterocycles, 14, 1980, 1145–1149.*
The Condensed Chemical Dictionary, 9th Ed., Gessner G. Hawley Ed., Van Nostrand, New York, p. 25.*
Hawley, Gessner, "The Condensed Chemical Dictonary", 1977, Van Nostrand, New York, p. 436.*
Streitwieser, A. and Heathcock, C.H., "Introduction to Organic Chemistry, 2nd Ed.", Macmillan, New York, 1981, p. 1061.*
UK Search Report for 1999CH102.
Aust. J. Chem., 1986, vol. 39 (3), p. 503–510.
Helv. Chim. Acta, 1974, vol. 57 (8), p. 2664–2678.
UK Search Report for 1999CH116.
J. Polym. Sci. Chem. Ed., 1982, vol. 206 (6), p. 1469–1487.
EPO Search Report.
Derwent Patent Family Abstract for DE 25 36 120.
Article, "Studies on Heterocyclic Colouring Matters" by B.L. Kaul, Helvetica Chemica Acta, vol. 57 (8), 1974, pp. 2264–2678.
J. Polymer Scii. A–1, 6, (1968), 2939–2943.
J. Organic Chemistry 31, (1966) 625–626.
Can. J. Chem, 48, (1965), 2612–2616.
L.B. Schein, "Electrophotography and Development Physics", Springer indexes only Series in Electrophysics 14, Springer Verlag, $2^{nd}$ Edition, 1992.
J.F. Hughes, "Electrostatics Powder Coating" Research Studies, John Wiley & Sons, indexes only 1984.

* cited by examiner

*Primary Examiner*—Mukund J. Shah
*Assistant Examiner*—Thomas McKenzie
(74) *Attorney, Agent, or Firm*—Susan S. Jackson; Scott E. Hanf

(57) ABSTRACT

New heterocyclic compounds are disclosed which are used as intermediates for the preparation of trans-thiazine-indigo pigments which are in part new compounds and can be used for the mass pigmentation of organic substrates. Also disclosed are different environmentally friendly water-based processes for the preparation of the new heterocyclic compounds and the corresponding pigments.

12 Claims, No Drawings

PROCESS FOR THE PREPARATION OF THIAZINE-INDIGO COMPOUNDS AND OF NEW INTERMEDIATES THEREFOR

BACKGROUND OF THE INVENTION

This invention relates to a new process of forming heterocyclic compounds and their use in the preparation of asymmetrical cis- or trans-thiazine-indigo compounds. This invention also relates to a new process of forming new cis- or trans-thiazine-indigo compounds containing further heterocyclic or carbonamido moieties. This invention also relates to a process of converting the cis-thiazine-indigo compounds into the trans-thiazine-indigo isomers, which are known to be pigments.

Thiazine-indigo compounds are an important series of pigments. Prior art processes for forming these pigments involve the reaction of certain o-aminomercapto-carbocyclic or -heterocyclic compounds with maleic acid or a derivative thereof in the presence of a solvent. Solvents useful for this purpose were either a carboxylic acid (which also acted to catalyze the reaction) or an inert polar aprotic solvent.

Thus, in DE 2 151 723 a process is described for making symmetrically substituted benzothiazine-indigo compounds wherein substituted ortho-aminomercapto-carbocyclic or -heterocyclic compounds are reacted with a maleic acid derivative in a carboxylic acid, e.g. acetic acid. By symmetrically substituted is meant that there is identical substitution on each of the benzothiazine rings.

In DE-OS 253 61 20 a process is described for making other symmetrically substituted benzothiazine-indigo compounds wherein substituted ortho-aminothiophenols are reacted with a maleic acid derivative in an inert polar aprotic solvent. It is alleged that the benzothiazine-indigo compounds so formed display improved pigmentary properties, e.g. brighter and cleaner shade over the compounds made in a carboxylic acid solution. However, they can only be produced in poor yield.

An improved process of forming thiazine-indigo pigments is also described in the international application WO 98/32800 A1.

There still remains a need to provide a further improved process of forming thiazine-indigo compounds, especially trans-thiazine-indigo pigments.

DESCRIPTION OF THE PREFERRED EMBODIMENTS

Accordingly, the invention provides in one of its aspects an environmentally friendly water-based process for the preparation of thiazine-indigo compounds according to the formula (I) and (II)

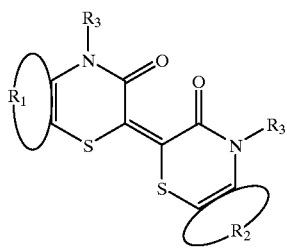

(I)

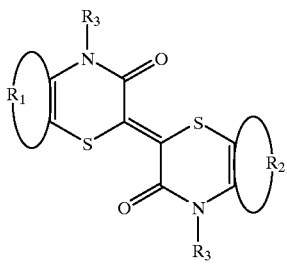

(II)

wherein $R_1$ and $R_2$ independently represent the atoms necessary to complete the formation of a substituted or unsubstituted aromatic or aliphatic carbocyclic or heterocyclic ring system and $R_3$ is hydrogen, $C_{1-12}$alkyl or phenyl, comprising the step of reacting in the presence of an aqueous system a compound of formula (Ia) resp. (Ib)

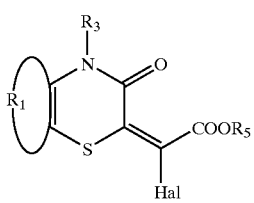

(Ia)

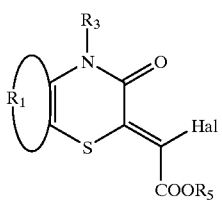

(Ib)

with a compound of formula (IIa)

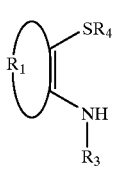

(IIa)

in which formulae $R_1$, $R_2$ and $R_3$ have the meaning indicated above; Hal is Cl or Br; $R_4$ is hydrogen or a metallic ion selected from $Na^+$, $K^+$ or $Zn^{2+}$ and $R_5$ is a leaving group commonly used in substitution reactions at carbonyl carbon atoms.

The aqueous system comprises water or water and an acidic catalyst or water and a basic catalyst or a mixture of water and a with water miscible solvent, like alcohols.

Preferably the molar ratio of the reactants is 1:1.

The process is carried out in the presence of a carboxylic acid or of a salt thereof, e.g. acetic acid, or an inorganic acid or salt thereof, e.g. sulphuric acid or hydrochloric acid, which also acts as a catalyst, and an aqueous medium, e.g. water or a mixture of water and a miscible solvent, preferably an alcohol with 1–5 C-atoms, e.g. ethanol, methanol, butanol or another high boiling point alcohol.

The basic catalyst is an inorganic base, especially sodium or potassium hydroxide or an organic base such as triethylamine.

The reaction is preferably carried out in water in the presence of 0 to 95% by weight, preferably 10% by weight of an acid catalyst, e.g. acetic acid or hydrochloric acid or sulphuric acid or phosphoric acid.

The reaction temperature is preferably of the order of 0 to 150° C., more preferably between 10 and 40° C.

The leaving group in $R_5$ is either hydroxy, chlorine or a $C_{1-5}$alkoxy group.

A further aspect of the invention consists in the process for the preparation of partly new compounds of the formula (Ia) and (Ib)

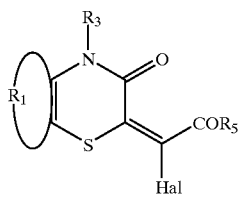

(Ia)

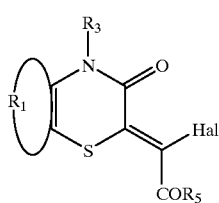

(Ib)

wherein the substituents $R_1$, $R_2$, $R_3$, $R_5$ and Hal have the meaning given above, comprising the reaction of a compound of formula (IIb)

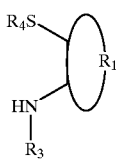

(IIb)

with a compound of formula (IIIa) or (IIIb)

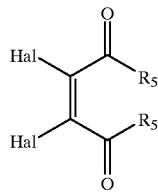

(IIIa)

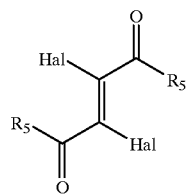

(IIIb)

wherein Hal is Cl or Br and $R_5$ is a leaving group commonly used in substitution reactions at carbonyl carbon atoms, in the same aqueous system as described above.

Compounds of formula (II), (IIIa) and (IIIb) are known compounds or can be prepared in analogy to known methods.

The compound of formula (IV)

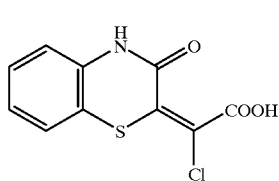

(IV)

is known and its preparation is described in Aust. J. Chem., 39, 503–510 (1986). However, the reaction is performed in organic solvents and the product was isolated in poor yield (28.8%) as a by-product.

The preparation of compound (IV) is also described in Helvetica Chem. Acta, 57 (8), 2664–78 (1974). Herein the reaction is carried out in glacial acetic acid.

The water based process of the invention is generally applicable and allows the preparation of other derivatives, in good yield.

The thiazine-indigo compounds of formula (I) or (II) may be symmetrically substituted, that is $R_1$ and $R_2$ are identical. Alternatively, they may be asymmetrically substituted, that is $R_1$ and $R_2$ are not identical. Non-identity refers to either the ring systems $R_1$ and $R_2$ being different or, in the event that the ring systems are identical, the substituents attached to the respective ring systems are different.

Preferred thiazine-indigo compounds formed according to the invention are those asymmetric compounds wherein $R_1$ and $R_2$ are independently selected from the group consisting of

(a)

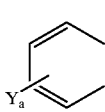

(b)

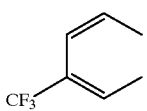

(c)

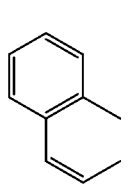

(d)

-continued

(e)

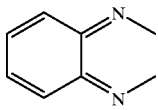
(f)

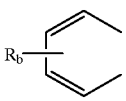
(g)

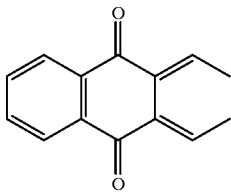
(h)

wherein Y is halogen which includes F, Cl and Br, especially Cl; R is $C_{1-4}$alkyl, especially methyl or ethyl, aryl, OR', SR', NR'R" or CONR'R", where R' and R" are independently H, $C_{1-18}$alkyl, $C_{5-10}$cycloalkyl or aryl; a is 1, 2, 3 or 4 and b is 1, 2, 3 or 4.

More preferred thiazine-indigo compounds are those in which $R_1$ consists of the atoms necessary to complete a benzene ring which is optionally substituted with, for example halogen or alkyl and $R_2$ consists of the atoms necessary to complete a ring system which is an equally substituted benzene ring or a different ring system, e.g. naphthalene, pyridine or 1,4-benzodiazine.

The thiazine-indigo compounds formed according to the invention may be substituted on the ring systems with one or more of any of the non-water-solubilising substituents common in the art of pigments. Preferably the ring system substituents are selected from the group consisting of halogen, trifluoromethyl, nitro, cyano, carbonamide, alkyl, aryl, alkoxy, amino, alkylamino, thioalkyl, phenoxy, phenylamino, phenylthio, acyl, acyloxy or acylamino.

The term "halogen" includes fluorine and especially chlorine and bromine. The term "alkyl" or "alkoxy" comprises preferably radicals with 1 to 4 carbon atoms. The terms "alkylamino" and "phenylamino" include for example N,N-dialkylamino and N,N-diphenylamino as well as N-monoalkylamino and N-monophenylamino.

The aforementioned alkyl, alkoxy, phenyl and phenoxy substituents may themselves contain one or more substituents selected from the substituents hereinabove described.

Another category of preferred thiazine-indigo compounds according to the invention are those of the formulae (I) and (II) in which $R_1$ and $R_2$ represent the atoms necessary to complete the formation of a benzene ring which is part of a heterocyclic ring system and more specifically compounds of the formulae (Va) resp. (Vb), (VIa) resp. (VIb), (VIIa) resp. (VIIb) and (VIIIa) resp. (VIIIb)

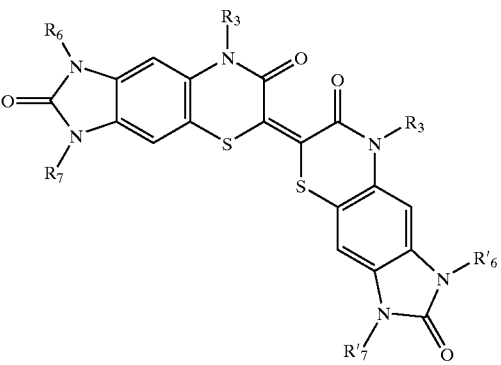
(Va)

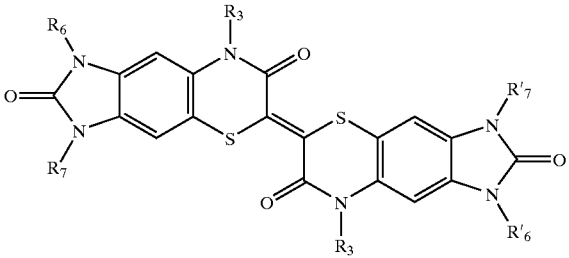
(Vb)

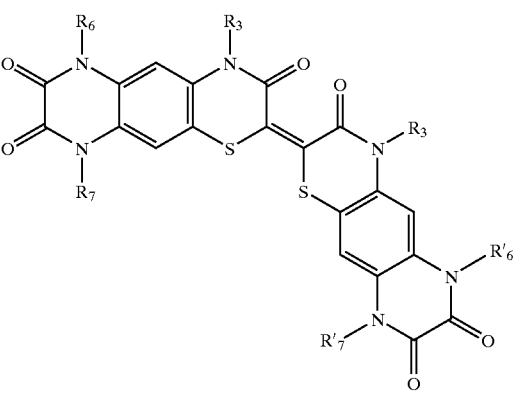
(VIa)

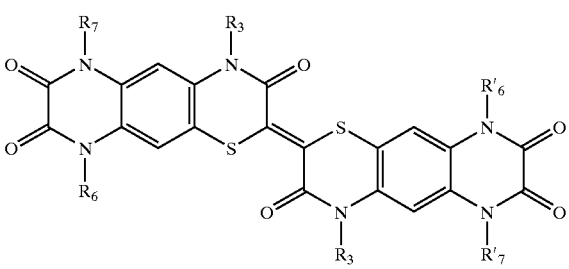
(VIb)

(VIIa)

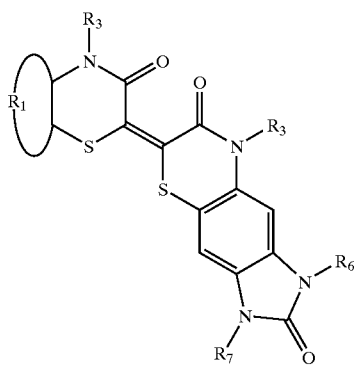

(VIIb)

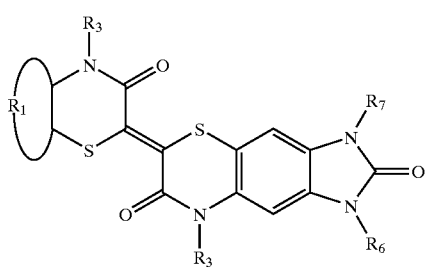

(VIIIa)

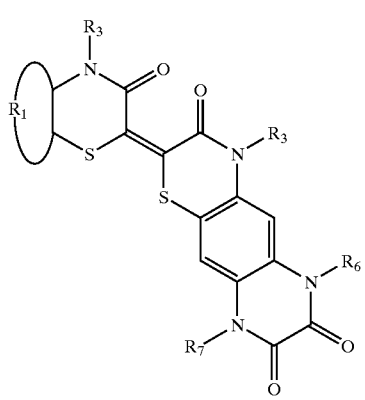

(VIIIb)

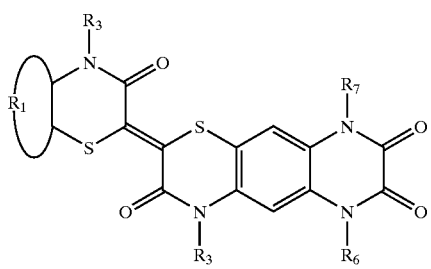

wherein R₁ represents the atoms necessary to complete the formation of a substituted or unsubstituted aromatic or aliphatic carbocyclic or heterocyclic ring system; $R_3$ is hydrogen, $C_{1-12}$alkyl or phenyl; $R_6$, $R'_6$, $R_7$ and $R'_7$ are independently hydrogen, an alkyl or aryl group which are novel compounds and can be prepared by a process comprising the step of reacting in the presence of an aqueous system a compound of formula (IXa) and/or (IXb)

(IXa)

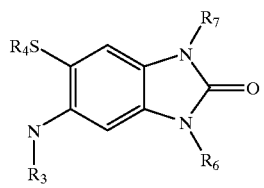

(IXb)

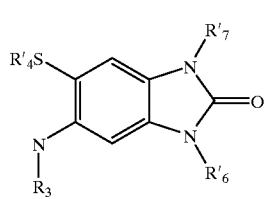

or a compound of formulae (Xa) and/or (Xb)

(Xa)

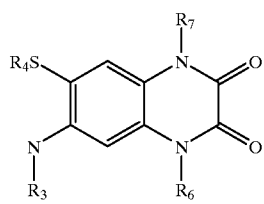

(Xb)

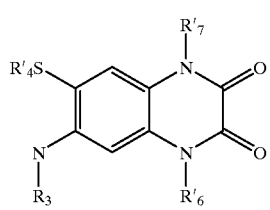

wherein $R_4$ and $R'_4$ independently are H or a metallic ion selected from $Na^+$, $K^+$ or $Zn^{2+}$ or a compound of formulae (IXa) or (Xa) and a compound of formula (IIb)

(IIb)

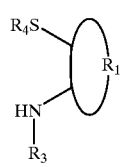

with a compound of formula (IIIa) [cis-isomers] or (IIIb) [trans-isomers]

(IIIa)

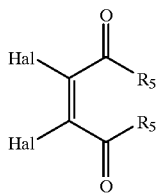

(IIIb)

wherein Hal is Cl or Br and $R_5$ is a leaving group commonly used in substitution reactions at carbonyl carbon atoms, e.g. Cl or $C_{1-5}$alkoxy or OH.

The aqueous system comprises water or water and an acidic catalyst or water and a basic catalyst or a mixture of water and a with water miscible solvent, like alcohols.

Particularly interesting is the possibility to use dihalofumaric acids or dihalomaleic acids, already prepared or generated in situ.

It has been discovered that fumaric derivatives of formula (IIIb) give the trans-isomer of formula (VIIb) or (VIIIb) and the maleic derivatives of formula (IIa) give the cis-isomer of formula (VIIa) or (VIIIa).

Preferably the molar ratio of the reactants is 2:1 respectively 1:1:1 when different compounds of formula (IXa), (IXb) or (Xa), (Xb) are used.

The process is carried out in the presence of a carboxylic acid or salt thereof, e.g. acetic acid, or an inorganic acid or salt thereof, e.g. sulphuric acid or hydrochloric acid, which also acts as a catalyst, and an aqueous medium, e.g. water or a mixture of water and a miscible solvent, preferably an alcohol with 1–5 C-atoms, e.g. ethanol, methanol, butanol or another high boiling point alcohol.

The basic catalyst is an inorganic base, especially sodium or potassium hydroxide or an organic base such as triethylamine.

The reaction is preferably carried out in water in the presence of 0 to 95% by weight, preferably 10% by weight of an acid catalyst, e.g. acetic acid or hydrochloric acid or sulphuric acid or phosphoric acid.

The reaction temperature is preferably of the order of 0 to 150° C., more preferably between 10 and 100° C. The pressure is preferably of the order of 1 to 20 bars, more preferably between 1 and 10 bars.

A further group of novel compounds are compounds of the formulae (XI) and (XII)

(XI)

(XII)

wherein $R_8$ and $R_9$ are independently H, $C_{1-18}$alkyl, phenyl, naphthyl, $C_{5-10}$cycloalkyl or Such compounds are prepared by the process according to the invention starting from the intermediates (XIII), (XIV) and (XV)

(XIII)

(XIV)

(XV)

wherein $R_8$ and $R_9$ are independently H, $C_{1-18}$alkyl, phenyl, naphthyl, $C_{5-10}$cycloalkyl or $R_4$ is H or a metallic ion selected from $Na^+$, $K^+$ or $Zn^{2+}$.

The compounds of formula (XIII) and (XIV), except for $R_8=R_9=H$, are new. They are prepared according to methods described in the literature (FR-patent 1443917). The compounds of formula (XIII) and (XIV) with $R_8=R_9=H$ are already published in J. Polymer Sci. A-1, 6, (1968), 2939.

Reduction of compounds of formula (XIII) and (XIV) forms compounds of formula (XV). According to methods described in the literature the reagent for reduction can be zinc in acetic acid (J. Org. Chem. 31, (1966), 625), or zinc with aqueous hydrochloride acid in an alcohol (in analogy to Can. J. Chem, 48, (1965), 2612) or sodium sulfide or sodium hydrogen sulfide.

Alternatively, the compounds of the invention which are trans-isomers can be prepared by reacting the starting materials in an inert polar solvent in the presence or not of an acidic catalyst which can be a carboxylic acid, e.g. acetic acid or p-toluene sulfonic acid.

A further aspect of the invention is the process of converting the cis-isomers into the trans-isomers by thermal treatment in an inert polar solvent, in the presence or not of an acidic catalyst, that can be a carboxylic acid, e.g. acetic acid, or para-toluene sulfonic acid or another acid usually used in organic chemistry.

The inert polar solvent can be chlorobenzene, nitrobenzene, dimethylformamide, dimethylacetamide, N-methylpyrrolidone, or a high boiling point alcohol, like ethylene glycol, dipropylene glycol methyl ether.

The cis-trans conversion can also be carried out in a mixture of water with a miscible alcohol at high temperature and under pressure.

The thermal treatment comprises temperatures of from 100 to 250° C., preferably of from 100 to 180° C., more preferably of from 130 to 160° C., and pressures of from 1 to 60 bars, preferably of from 1 to 20 bars.

The trans-thiazine-indigo pigments formed by the conversion process according to the invention are suitable for the mass pigmentation of suitable substrates including synthetic polymers, synthetic resins and regenerated fibers optionally in the presence of solvents. These substrates more particularly include oil, water and solvent based surface coatings, polyester spinning melts, polyethylene, polystyrene and polyvinyl chloride molding materials, rubber and synthetic leather. Furthermore, the pigments can be used in the manufacture of printing inks, for the mass coloration of paper and for coating and printing textiles.

The trans-thiazine-indigo pigments are also suitable for cosmetic uses, like nail varnishes or make-up.

The trans-thiazine-indigo pigments are also suitable as colorants in electrophotographic toners and developers, such as one- or two-component powder toners (also called one- or two-component developers), magnetic toners, liquid toners, polymerization toners and specialty toners (literature: L. B. Schein, "Electrophotography and Development Physics"; Springer Series in Electrophysics 14, Springer Verlag, $2^{nd}$ Edition, 1992).

Typical toner binders are addition polymerization, polyaddition and polycondensation resins, such as styrene, styrene-acrylate, styrene-butadiene, acrylate, polyester and phenol-epoxy resins, polysulphones, polyurethanes, individually or in combination, and also polyethylene and polypropylene, which may comprise further constituents, such as charge control agents, waxes or flow assistants, or may be modified subsequently with these additives.

The trans-thiazine-indigo pigments are suitable, furthermore, as colorants in powders and powder coating materials, especially in triboelectrically or electrokinetically sprayable powder coating materials which are used for the surface coating of articles made, for example, from metal, wood, plastic, glass, ceramic, concrete, textile material, paper or rubber (J. F. Hughes, "Electrostatics Powder Coating" Research Studies, John Wiley & Sons, 1984).

Powder coating resins that are typically employed are epoxy resins, carboxyl- and hydroxyl-containing polyester resins, polyurethane resins and acrylic resins, together with customary hardeners. Combinations of resins are also used. For example, epoxy resins are frequently employed in combination with carboxyl- and hydroxyl-containing polyester resins. Typical hardener components (as a function of the resin system) are, for example, acid anhydrides, imidazoles and also dicyanodiamide and its derivatives, blocked isocyanates, bisacylurethanes, phenolic and melamine resins, triglycidyl isocyanurates, oxazolines and dicarboxylic acids.

In addition, the trans-thiazine-indigo pigments are suitable as colorants in ink-jet inks, both aqueous and non-aqueous, and in those inks which operate in accordance with the hot-melt process.

Based on the substrate to be mass pigmented the thioazine-indigo pigments according to the invention are used in amounts of 0.01 to 30% by weight, preferably 0.1 to 10% by weight.

When applied to the afore-mentioned substrates the thiazine-indigo pigments are found to be resistant to migration and fast to light, and show fastness to washing, chlorite, hypochlorite and peroxide bleaching, rubbing, overspraying and solvents. Notably, the pigments display high tinctorial power, good transparency and good heat stability.

EXAMPLES

The invention is further illustrated by means of the following examples in which all percentages and all quantities are expressed by weight.

Example 1

166.25 g of o-aminothiophenol (1.33 mole) are dropped at 20° C. during 5 hours into a solution of 259 g of 2,3-dichloromaleic acid (1.4 mole) in 1750 ml of water containing 7 ml of the dispersing agent Sandopan 2 N, under a nitrogen atmosphere. A yellow precipitate rapidly appears. The mixture is stirred overnight at room temperature. The suspension is then filtered and washed out with 4000 ml of water. The product is then dried at 80° C. under vacuum overnight. 285.9 g of a yellow product is obtained, 84.1%. This product is the compound of the following formula and is soluble in polar organic solvent.

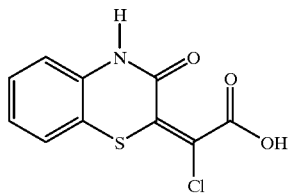

MS (API-ES, negative ionization): m/z=254 [M−H]$^+$; 210 (—$CO_2$)

Example 2

A reactor is charged with 101.2 g of 30% concentrated sodium hydroxide, 38.85 g of sodium hydroxide, 92.25 g of 2-amino-6-chlorobenzothiazole. The mixture is then heated at reflux for 24 hours. After that, the mixture is allowed to cool at 20° C., diluted with 150 ml of water. 122.9 g of sulfuric acid 50% are dropped into the reactor to reach pH 8.7. Another reactor is charged with 92.5 g of dichloromaleic acid, 200 ml of water, and 2 ml of the dispersing agent Sandopan 2N. The sodium 2-amino-5-chlorothiophenolate of the first reactor is then added to the content of the second reactor during 2 hours. A yellow solid is formed, and then the reaction mixture is stirred overnight at 20° C. The yellow suspension is filtered and washed out with 2 liters of water.

The product is then dried at 80° C. under vacuum overnight. 281.4 g of a yellow product is obtained, 75.4%. This product is the compound of the following formula:

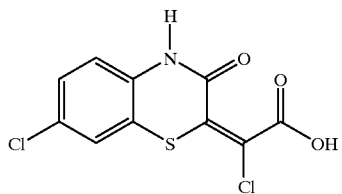

MS (API-ES, negative ionization): m/z=288 [M−H]$^+$; 244 (—$CO_2$)

Example 3

A 1 liter reactor is charged with 300 ml of ethanol, 68.7 g of zinc powder and 60 g of bis(4-carbonamide-2-nitrophenyl) disulfide. The mixture is heated to 70° C. and then 230 g of 35% concentrated hydrochloric acid are added during one hour. The mixture is stirred at 70° C. for 2 hours and 48 g more of concentrated hydrochloric acid are added. The solution is cooled to 40° C. and 76.65 g of the compound described in the example 1 are added into the reactor and after 30 min. the mixture is heated to reflux and stirred overnight at this temperature. The solid product is filtered hot and washed with 800 ml of hot ethanol and 2000 ml of hot water.

The product is then dried at 80° C. under vacuum overnight. 70.8 g of a brownish red product is obtained. This product is the compound of the following formula:

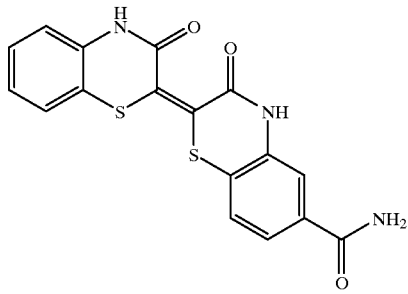

Example 4

A 1 liter reactor is charged with 300 ml of ethanol, 68.7 g of zinc powder and 60 g of bis(4-carbonamide-2-nitrophenyl) disulfide. The mixture is heated to 70° C. and then 230 g of 35% concentrated hydrochloric acid are added during one hour. The mixture is stirred at 70° C. for 2 hours and 48 g more of concentrated hydrochloric acid are added. The solution is cooled to 45° C. and 87 g of the compound described in the example 2 are added into the reactor and after 30 min. the mixture is heated to reflux and stirred overnight at this temperature. The solid product is filtered hot and washed with 800 ml of hot ethanol and 2000 ml of hot water.

The product is then dried at 80° C. under vacuum overnight. 72.1 g of a brownish red product is obtained. This product is the compound of the following formula:

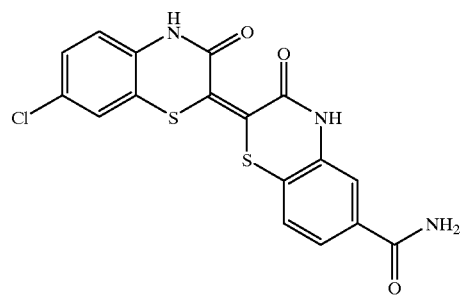

Example 5

Isomerization of a cis-thiazine-indigo Compound into the trans-thiazine-indigo Pigment 70 g of the compound prepared in the example 3 are dispersed in 280 ml of dimethylacetamide and 3 ml of acetic acid, then heated to 145° C. for 16 hours. The isomerisation occurs during this thermal treatment, the initial yellowish orange suspension becomes red and thicker. The pigment is then filtered at 100° C. washed with 600 ml of dimethylacetamide and 300 ml of ethanol. The product is dried at 80° C. under vacuum overnight. 48.5 g of a red orange solid being the trans-thiazine-indigo isomer of the following formula

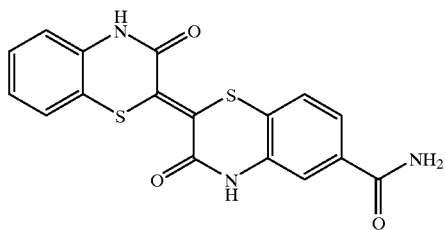

is obtained.

Example 6

Isomerization of a cis-thiazine-indigo Compound into the trans-thiazine-indigo Pigment 69 g of the compound prepared in the example 4 are dispersed in 350 ml of dimethylacetamide and 3 ml of acetic acid, then heated to 145° C. for 16 hours. The isomerisation occurs during this thermal treatment, the initial yellowish orange suspension becomes red and thicker. The pigment is then filtered at 100° C. washed with 600 ml of dimethylacetamide and 300 ml of ethanol. The product is dried at 80° C. under vacuum overnight. 51 g of a red orange solid being the trans-thiazine-indigo isomer of the following formula

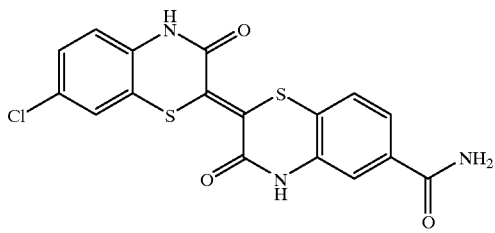

is obtained.

Example 7

A reactor is charged with 144 g of 30% concentrated sodium hydroxide, 56 g of sodium hydroxide, 103 g of 2-amino-5,7-dihydro-imidazo[4',5':4,5]benzo[1,2-d]thiazol-6-one. The mixture is then heated at reflux for 24 hours. After that, the mixture is allowed to cool at 20° C., diluted with 200 ml of water. 196 g of 50% concentrated sulfuric acid are dropped into the reactor. Another reactor is charged with 46.2 g of dichloromaleic acid, 300 ml of water and 2 ml of the dispersing agent Sandopan 2N. The sodium 2-amino-5,7-dihydro-imidazo[4',5':4,5]benzo[1,2-d]thiophenolate-6-one of the first reactor is then added to the content of the second reactor during one hour. The pH is maintained to 1 during the addition by dropping 65 g of 50% concentrated sulfuric acid. An orange solid is formed, and then the reaction mixture is heated to reflux for 24 hours. The orange suspension is filtered hot and washed out with 1.2 liters of hot water. The product is dried at 80° C. under vacuum overnight. 110.5 g of a dried crude product of the following formula

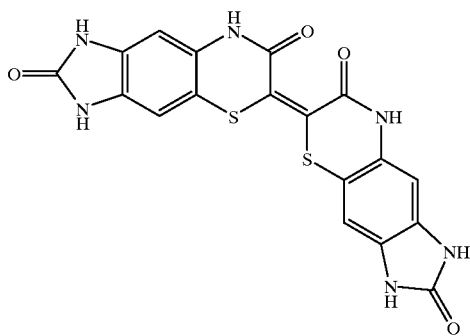

is obtained.

Example 8

The crude product obtained in the example 7 is slurried in 500 ml of dimethylacetamide and 2 ml of acetic acid. The mixture is heated at 150° C. for 12 hours. The mixture becomes red, indicating that the cis to trans conversion takes place. The red brown solid is then filtered hot, washed with 500 ml of hot dimethylacetamide and 150 ml of ethanol. The product is dried at 80° C. under vacuum overnight. 23.1 g of pigment of the following formula

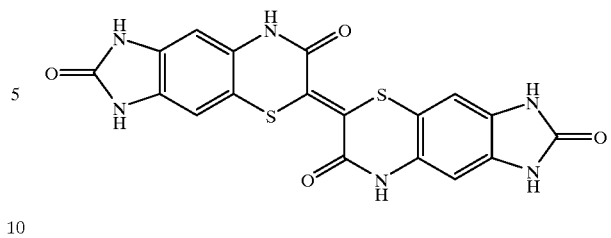

are obtained.

$^1$H-NMR (300 MHz, D$_6$-DMSO): δ=6.65 (s,2H); 6.80 (s, 2H); 10.60 (s, 2H); 10.65(s, 2H); 10.90 (s, 2H)

Example 9

A reactor is charged with 180 g of 30% concentrated sodium hydroxide, 70 g of sodium hydroxide, 110 g of 2-amino-5-hydro-7-methyl-imidazo[4',5':4,5]benzo[1,2-d]thiazol-6-one. The mixture is then heated at reflux for 24 hours. After that, the mixture is allowed to cool at 20° C., diluted with 214 ml of water. 209.4 g of 50% concentrated sulfuric acid are dropped into the reactor. Another reactor is charged with 46.22 g of dichloromaleic acid, 340 ml of water and 2 ml of the dispersing agent Sandopan 2N. The sodium 2-amino-5-hydro-7-methyl-imidazo[4',5':4,5]benzo[1,2-d]thiophenolate-6-one of the first reactor is then added to the content of the second reactor during one hour. The pH is maintained to 1 during the addition by dropping 120 g of 50% concentrated sulfuric acid. An orange-brown solid is formed, and then the reaction mixture is heated to reflux for 24 hours. The orange-brown suspension is filtered hot and washed out with 1.7 liters of hot water. The product is dried at 80° C. under vacuum overnight. 119 g of a dried crude product of the formula

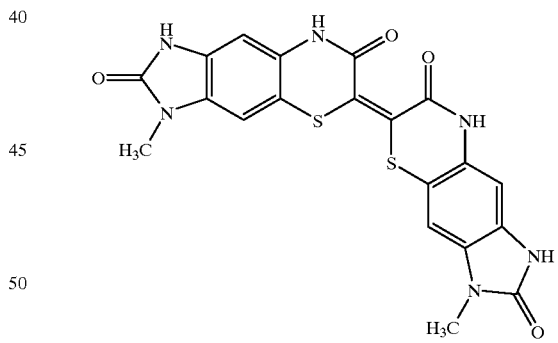

are obtained.

Example 10

The product of the example 9 is slurried in 460 ml of dimethylacetamide and 2.3 ml of acetic acid. The mixture is heated at 150° C. for 12 hours. The mixture becomes red, indicating that the cis to trans conversion takes place. The red-brown solid is then filtered hot, washed with 300 ml of hot dimethylacetamide and 150 ml of ethanol. The product is dried at 80° C. under vacuum overnight. 43.1 g of pigment of the following formula

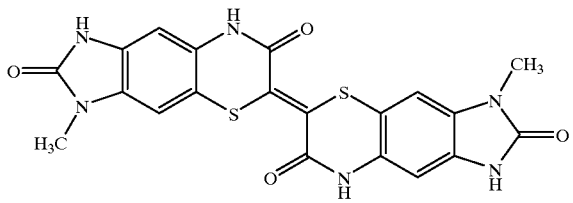

are obtained.

$^1$H-NMR (300 MHz, D$_6$-DMSO): δ=3.15 (s, 6H); 6.80 (s, 2H); 7.20 (s, 2H); 10.85 (s, 2H); 11.25 (s, 2H)

Example 11

A reactor is charged with 180 g of 30% concentrated sodium hydroxide, 70 g of sodium hydroxide, 117 g of 2-amino-5-hydro-7-ethyl-imidazo[4',5':4,5]benzo[1,2-d]thiazol-6-one. The mixture is then heated at reflux for 24 hours. After that, the mixture is allowed to cool at 20° C., diluted with 227 ml of water. 222.7 g of 50% concentrated sulfuric acid are dropped into the reactor. Another reactor is charged with 46.22 g of dichloromaleic acid, 342 ml of water and 2 ml of the dispersing agent Sandopan 2N. The sodium 2-amino-5-hydro-7-ethyl-imidazo[4',5':4,5]benzo[1,2-d]thiophenolate-6-one of the first reactor is then added to the content of the second reactor during one hour. The pH is kept near to 1 during the addition by dropping 100 g of 50% concentrated sulfuric acid. An orange-brown solid is formed, and then the reaction mixture is heated to reflux for 24 hours. The orange-brown suspension is filtered hot and washed out with 1.7 liters of hot water. The product is dried at 80° C. under vacuum overnight. 124.8 g of a dried crude product of the following formula

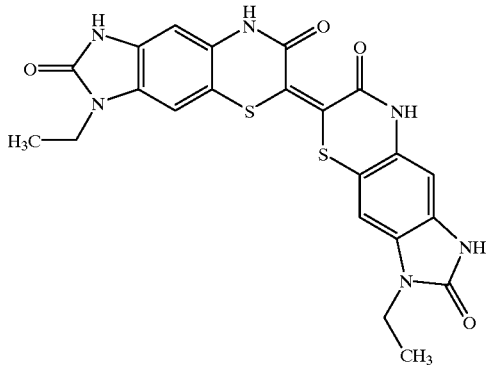

are obtained.

Example 12

This crude product obtained in the example 11 is reslurried in 480 ml of dimethylacetamide and 2.4 ml of acetic acid. The mixture is heated at 150° C. for 12 hours. The mixture becomes red, indicating that the cis to trans conversion takes place. The red-brown solid is then filtered hot, washed with 300 ml of hot dimethylacetamide and 150 ml of ethanol. The product is dried at 80° C. under vacuum overnight. 39.1 g of pigment of the following formula

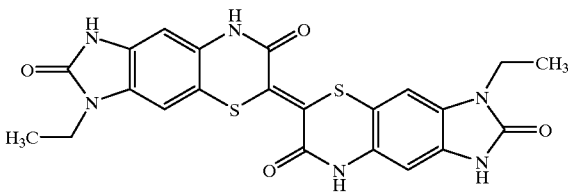

are obtained.

Example 13

A reactor is charged with 72 g of 30% concentrated sodium hydroxide, 28 g of sodium hydroxide, 16.13 g of 2-amino-5,7-dihydro-imidazo[4',5':4,5]benzo[1,2-d]thiazol-6-one. The mixture is then heated at reflux for 24 hours. After that, the mixture is allowed to cool at 20° C., diluted with 54 ml of water. 15 g of 50% concentrated sulfuric acid are dropped into the reactor. Another reactor is charged with 20 g of the product of example 1, 200 ml of water and 2 ml of the dispersing agent Sandopan 2N. The sodium 2-amino-5,7-dihydro-imidazo[4',5':4,5]benzo[1,2-d]thiophenolate-6-one of the first reactor is then added to the content of the second reactor during one hour. The pH is kept near to 1 during the addition by dropping 24 g of 50% concentrated sulfuric acid. An orange solid is formed, and then the reaction mixture is heated to reflux for 24 hours. The orange suspension is filtered hot and washed out with 1.3 liters of hot water. The product is dried at 80° C. under vacuum overnight. 28.4 g of a dried crude product of the formula

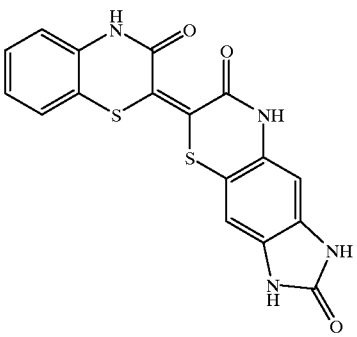

are obtained.

Example 14

This crude product obtained in the example 13 is slurried in 104 ml of dimethylacetamide and 0.5 ml of acetic acid. The mixture is heated at 150° C. for 12 hours. The mixture becomes red, indicating that the cis to trans conversion takes place. The red solid is then filtered hot, washed with 250 ml of hot dimethylacetamide and 100 ml of ethanol. The product is dried at 80° C. under vacuum overnight. 11.7 g of pigment of the following formula

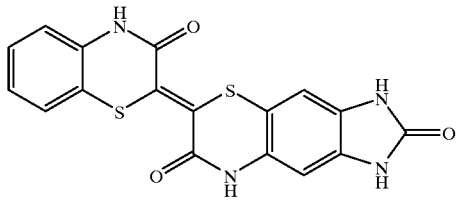

are obtained.

¹H-NMR (300 MHz, D₆-DMSO): δ=6.65 (s, 1H); 6.75 (s, 1H); 7.00, (m, 2H); 7.18 (m, 1H); 7.25 (m, 1H); 10.60 (s, 1H); 10.65 (s, 1H); 11.00 (s, 1H); 11.15 (s, 1H)

Example 15

A reactor is charged with 42.48 g of 30% concentrated sodium hydroxide, 16.52 g of sodium hydroxide, 30.2 g of 2-amino-5-hydro-7-ethyl-imidazo[4',5':4,5]benzo[1,2-d] thiazol-6-one. The mixture is then heated at reflux for 24 hours. After that, the mixture is allowed to cool at 20° C., diluted with 59 ml of water. 57.5 g of 50% concentrated sulfuric acid are dropped into the reactor. Another reactor is charged with 30 g of the product of example 1, 300 ml of water and 2 ml of the dispersing agent Sandopan 2N. The sodium 2-amino-5-hydro-7-ethyl-imidazo[4',5':4,5]benzo[1, 2-d]thiophenolate-6-one of the first reactor is then added to the content of the second reactor during one hour. The pH is kept near to 1 during the addition by dropping 26 g of 50% concentrated sulfuric acid. An orange solid is formed, and then the reaction mixture is heated to reflux for 24 hours. The orange suspension is filtered hot and washed out with 1.6 liters of hot water. The product is dried at 80° C. under vacuum overnight. 52.1 g of a dried crude product of the formula

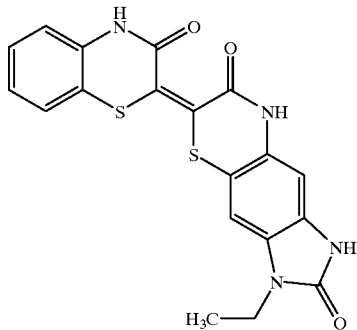

are obtained.

Example 16

This crude product obtained in the example 15 is slurried in 200 ml of dimethylacetamide and 1 ml of acetic acid. The mixture is heated at 150° C. for 12 hours. The mixture becomes red, indicating that the cis to trans conversion takes place. The red solid is then filtered hot, washed with 350 ml of hot dimethylacetamide and 150 ml of ethanol. The product is dried at 80° C. under vacuum overnight. 16.1 g of pigment of the following formula

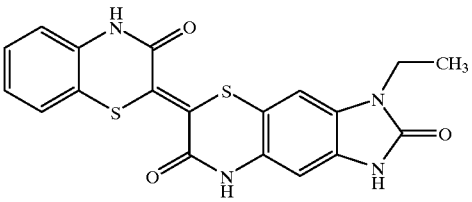

are obtained.

¹H-NMR (300 MHz, D₆-DMSO): δ=0.85, (t, 3H); 1.08 (m, 2H); 6.25 (s, 1H); 6.35 (s, 1H); 7.05–7.10 (m, 2H); 7.15–7.18 (m, 1H); 7.20–7.25 (m, 1H); 10.80 (s, 1H); 10.85 (s, 1H); 11.00 (s, 1 H)

Example 17

A 6-liter reactor is charged with 900 ml of ethanol, 302 g of zinc powder and 363 g of 4-mercapto-3-nitro-N-phenyl-benzamide. The mixture is heated to 65° C. and then 992 g of 34% concentrated hydrochloric acid are added within two hours while maintaining the reaction temperature below 70° C. The mixture is stirred at reflux for 2.5 hours and 50 g more of concentrated hydrochloric acid are added. A white suspension is formed. The reaction mixture is cooled to 70° C., filtered hot, and washed with 26 liters of water. The white product is dried at 80° C. under vacuum overnight. 264.6 g (72.6%) of 4-mercapto-3-nitro-N-phenyl-benzamide zinc salt are obtained.

A 2-liter reactor is charged with 792 g of dimethylacetamide, 88.4 g of dichloromaleic acid and 80 g of acetic acid. 264 g of the prepared 4-mercapto-3-nitro-N-phenyl-benzamide zinc salt are added over 45 mn at room temperature. The white suspension is heated within 3 hours to 65° C. and is stirred at that temperature overnight. The suspension becomes orange. The reaction mixture is then heated gradually to 145° C. over a period of 8 hours and is stirred at that temperature for a further night. The solid product is filtered hot (100° C.), washed with 1100 ml of hot dimethylacetamide, and with 3 liters of hot water. The product is dried at 80° C. under vacuum over night. 137.4 g (51%) of a brilliant reddish yellow solid product are obtained. This product is the compound of the following formula:

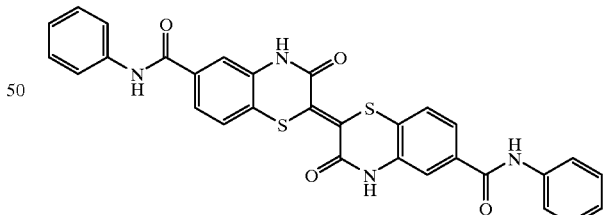

¹H-NMR (300 MHz, D₆-DMSO/NaOD): δ=6.54 (t, 2H); 6.68 (d, 2H); 6.98 (t, 4H); 7.25 (dd, 2H); 7.32 (m, 6H). calculated: C, 63.8%; H, 3.6%; N, 9.9%; S, 11.4%; O, 11.3% found: C, 62.7%; H, 3.4%; N, 10.3%; S, 11.1%; O, 11.2%.

Example 18

A 1-liter reactor is charged with 610 ml of ethanol, 91.6 g zinc powder and 136.8 g of 4-mercapto-3-nitro-N-(4-trifluoromethylphenyl)-benzamide. The mixture is heated to 65° C. and then 301 g of 34% concentrated hydrochloric acid are added within one hour while maintaining the reaction temperature below 70° C. The mixture is stirred at 70° C. for 2.5 hours and 30 g more of concentrated hydrochloric acid are added. The brownish yellow solution is cooled to 70° C.

Another reactor is charged with 37.0 g of dichloromaleic acid, 100 ml of water and 1 ml of the dispersing agent Sandopan 2N. The mixture is heated to 40° C. The brownish yellow of the first reactor is then added to the content of the second reactor within 2.5 hours by passing a fritter (No. 3) to filter off remaining zinc particulates. The formed brownish orange suspension is heated up gradually within 5 hours to reflux and is stirred at this temperature overnight. The orange suspension is filtered hot, washed with 450 ml of hot ethanol, and with 12 l of water. The product is dried at 80° C. under vacuum overnight. 111.2 g (79.4%) of a orange product are obtained. This product is the compound of the following formula:

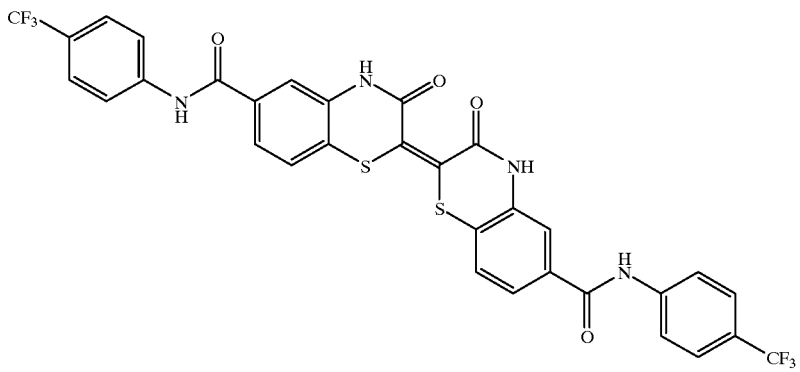

Example 19

56.1 g of the compound prepared in the example 18 are dispersed in 168.3 g of dimethylacetamide and 0.6 g of acetic acid, then heated to 145° C. for 24 hours. The pigment is filtered at 100° C., washed with 250 ml of hot dimethylacetamide, and 1000 ml of hot water. The product is dried at 80° C. under vacuum overnight. 39 g (69.5%) of a brilliant reddish orange solid product are obtained. This product is the compound of the following formula:

$^1$H-NMR (300 MHz, D$_6$-DMSO/NaOD): δ=6.71 (d 2H); 6.81 (dd, 2H); 7.16 (t, 2H); 7.27 (dd, 2H); 7.39 (d, 2H), 7.53 (d, 2H), 7.88 (s, 2H). calculated: C,54.9%; H, 2.6%; N, 8.0%; S, 9.1%. found: C, 54.6%; H, 2.4%; N, 8.3%; S, 9.1%.

Application Example 1

The preparation of a 0.1% colored PVC sheet is performed by following procedure: 100 parts of clear PVC are mixed with 0.1 part of pigment obtained in example 17 for 10 minutes. The mixture is passed between two rollers for 1 minute at 130° C. and then plastified for 7 minutes. Afterwards the sheet is pressed under a pressure of 20–30 bar between metal plates heated at 160° C. for 5 minutes. The pressed sheet is colored with a reddish yellow and transparent shade.

Application Example 2

The preparation of a 0.1% colored PVC sheet is performed by following procedure: 100 parts of clear PVC are mixed with 0.1 part of pigment obtained in example 19 for 10 minutes. The mixture is passed between two rollers for 1 minute at 130° C. and then plastified for 7 minutes. Afterwards the sheet is pressed under a pressure of 20–30 bar between metal plates heated at 160° C. for 5 minutes. The pressed sheet is colored with a reddish yellow and transparent shade.

Application Example 3

The preparation of the AM5 lacquer resin coating containing 4% of pigment is performed by the following procedures: 3.6 parts of pigments obtained in example 17, 26.4 parts of AM5-35% lacquer and 85 parts of glass beads are stirred in a Skandex stirrer for 30 minutes. After dispersion 60 parts of AM5-55.8% lacquer are added and the mixture

23 is stirred in a Skandex stirrer for further 3 minutes. The glass beads are filtered off. The dispersion is sprayed on a cardboard sheet, air-dried for 10 minutes and baked at 130° C. in an oven for 30 minutes. This gives a reddish yellow and transparent shade.

Application Example 4

The preparation of the AM5 lacquer resin coating containing 4% of pigment is performed by the following procedures: 3.6 parts of pigments obtained in example 19, 26.4 parts of AM5-35% lacquer and 85 parts of glass beads are stirred in a Skandex stirrer for 30 minutes. After dispersion 60 parts of AM5-55.8% lacquer are added and the mixture is stirred in a Skandex stirrer for further 3 minutes. The glass beads are filtered off. The dispersion is sprayed on a cardboard sheet, air-dried for 10 minutes and baked at 130° C. in an oven for 30 minutes. This gives a reddish yellow and transparent shade.

Application Example 5

The preparation of a 1% colored PVC sheet is performed following the DIN 5377A procedure: 100 parts of clear PVC are mixed with 1 part of pigment obtained in example 8 for 2 minutes. The mixture is passed between two rollers for 5 minutes, the front roller being heated at 178° C. and the rear roller being heated at 163° C. The PVC sheet is then treated again between the two rollers heated at 80° C. Then the sheet is pressed under a pressure of 30 tonnes between chromium-plated steel plates heated at 165° C., for 30 seconds. The pressed sheet is colored with a brown shade.

Application Example 6

The preparation of a 1% colored PVC sheet is performed following the DIN 5377A procedure: 100 parts of clear PVC are mixed with 1 part of pigment obtained in example 12 for 2 minutes. The mixture is passed between two rollers for 5 minutes, the front roller being heated at 178° C. and the rear roller being heated at 163° C. The PVC sheet is then treated again between the two rollers heated at 80° C. Then the sheet is pressed under a pressure of 30 tonnes between chromium-plated steel plates heated at 165° C., for 30 seconds. The pressed sheet is colored with a bluish red shade.

Application Example 7

The preparation of the alkydmelanine-formaldehyde (AM/F) resin coating is performed following the DIN 53235-1, DIN 8780/2 and 8781/1 procedures: 8 parts of pigments obtained in example 6, 72 parts of clear AM/F (BASF FF68-0102 14071) and 250 parts of glass beads are stirred in a Skandex stirrer for 10 minutes. 5 parts of this preparation are mixed with 5 parts of clear AM/F. The dispersion is sprayed on a cardboard sheet, air-dried for 10 minutes and baked at 130° C. in an oven for 30 minutes. This gives a bright red and transparent shade.

What is claimed is:

1. A process for the preparation of thiazine-indigo compounds according to the formula (Va) resp. (Vb), (VIa) resp. (VIb), (VIIa) resp. (VIb) and (VIIIa) resp. (VIIb)

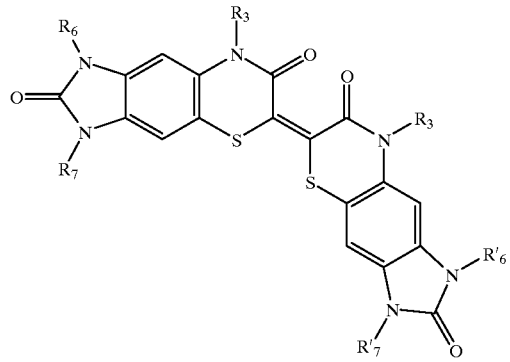

(Va)

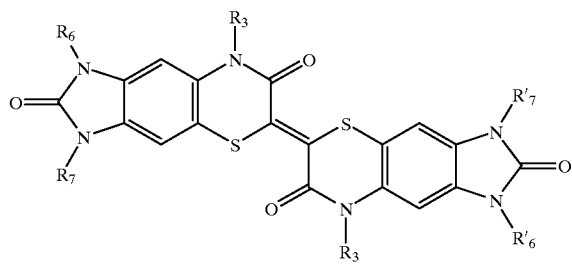

(Vb)

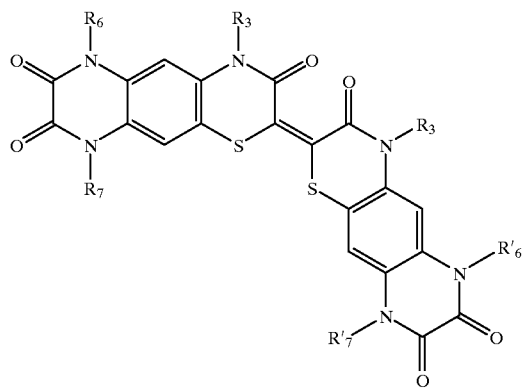

(VIa)

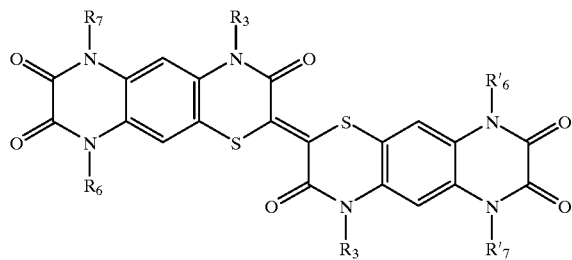

(VIb)

(VIIa)

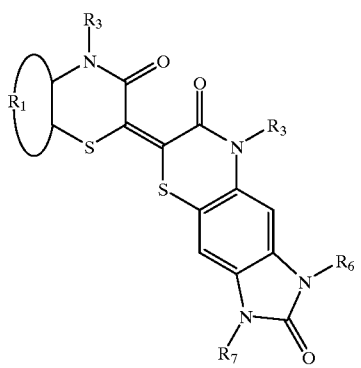

(VIIb)

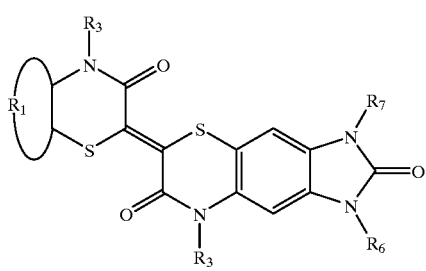

(VIIIa)

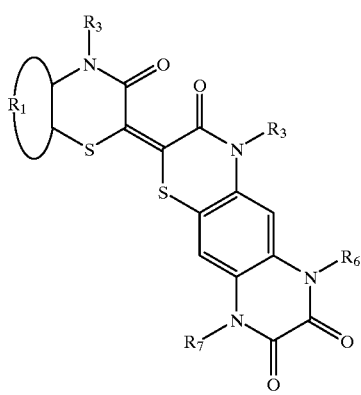

(VIIIb)

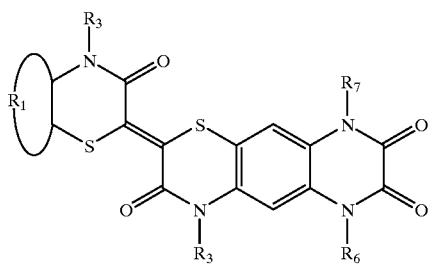

wherein $R_1$ represents the atoms necessary to complete the formation of a substituted or unsubstituted aromatic or alicyclic or heterocyclic ring system, wherein the heterocyclic ring system is a 6-membered N-heteroaromatic ring with one or two N atoms, optionally bearing a fused benzene ring or a benzene ring bearing a fused 5- or 6-membered N-heterocyclic ring with two N atoms; $R_3$ is hydrogen, $C_{1-12}$alkyl or phenyl; $R_6$, $R'_6$, $R_7$ and $R'_7$ are independently an hydrogen, alkyl or aryl group
comprising the step of reacting in the presence of an aqueous system a compound of formula (IXa) and/or (IXb)

(IXa)

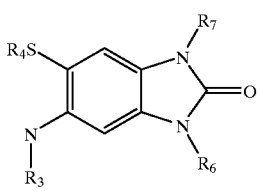

(IXb)

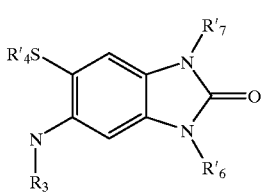

or a compound of formula (Xa) and/or (Xb)

(Xa)

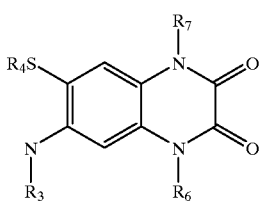

(Xb)

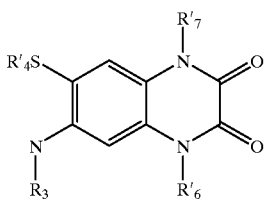

wherein $R_4$ and $R'_4$ independently are H or a metallic ion selected from $Na^+$, $K^+$ or $Zn^{2+}$ or a compound of formulae (IXa) or (Xa) and a compound of formula (IIb)

(IIb)

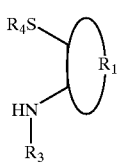

with a compound of formula (IIIa) (cis-isomers) or (IIIb) (trans-isomers)

(IIIa)

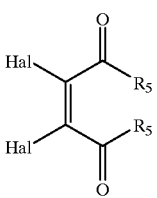

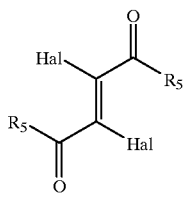

(IIIb)

wherein Hal is Cl or Br and $R_5$ is a leaving group commonly used in substitution reactions at carbonyl carbon atoms, e.g. Cl or $C_{1-5}$alkoxy or OH.

2. A process according to claim 1 wherein the aqueous system comprises water or water and an acidic catalyst or water and a basic catalyst or a mixture of water and a water miscible solvent.

3. A process according to claim 2 wherein the acidic catalyst is a carboxylic acid or an inorganic acid or salts thereof.

4. A process according to claim 2 wherein the with water miscible solvent is an alcohol with 1–5 C-atoms, preferably selected from the group consisting of methanol, ethanol and butanol.

5. A process according to claim 2 wherein the basic catalyst is selected from the group consisting of sodium hydroxide, potassium hydroxide and triethylamine.

6. A process of converting a cis-thiazine-indigo compound of formulae (Va), (VIa), (VIIa) or (VIIIa)

(Va)

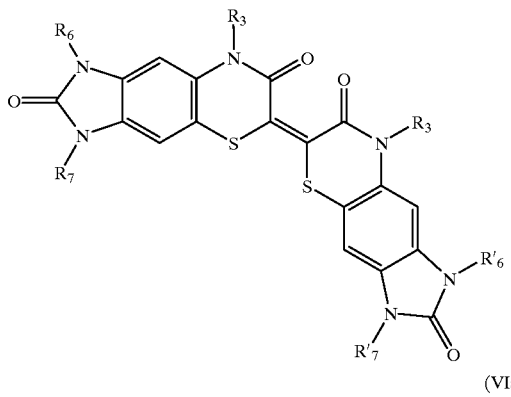

(VIa)

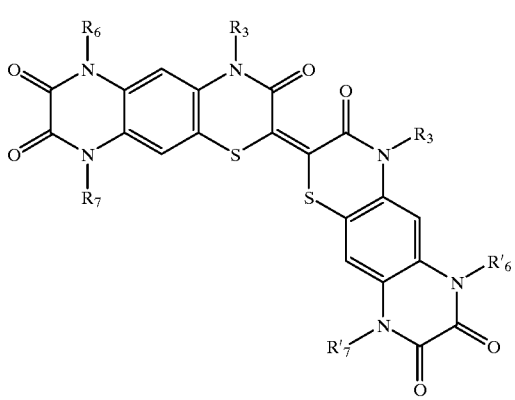

(VIIa)

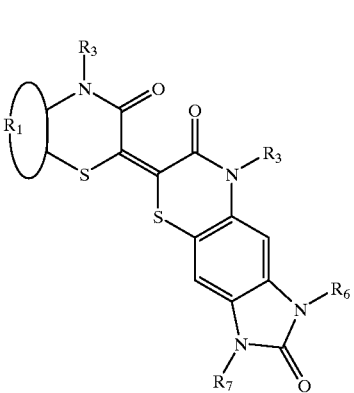

(VIIIa)

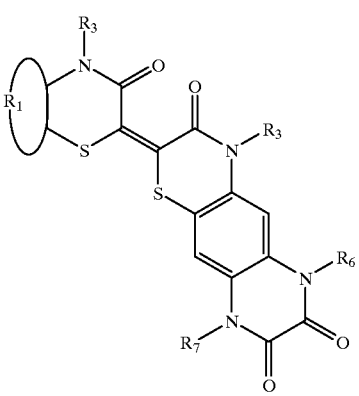

into the respective trans-thiazine-indigo pigment of formulae (Vb), (VIb), (VIIb) or (VIIIb)

(Vb)

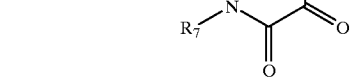

(VIb)

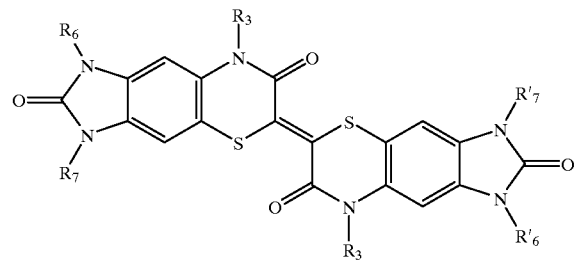

(VIIb)

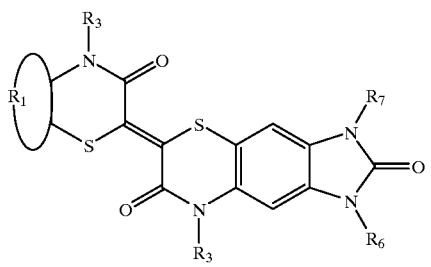

(VIIIb)

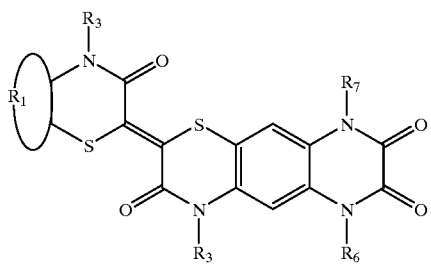

wherein $R_1$, $R_3$, $R_6$, $R'_6$, $R_7$ and $R'_7$ are defined according to claim 3, by thermal treatment in an inert polar solvent, optionally in the presence of an acidic catalyst, wherein the inert polar solvent is selected from the group consisting of dimethylformamide, dimethylacetamide, and N-methylpyrrolidone.

7. A process according to claim 6 wherein the thermal treatment comprises temperatures of from 100 to 250° C.

8. Thiazine-indigo compounds according to the formula (Va) resp. (Vb), (VIa) resp. (VIb), (VIIa) resp. (VIb) and (VIIIa) resp. (VIIb)

(Va)

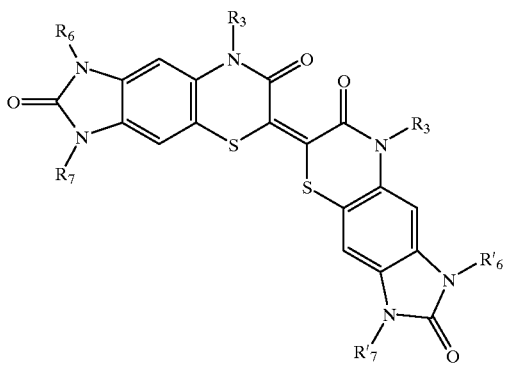

(Vb)

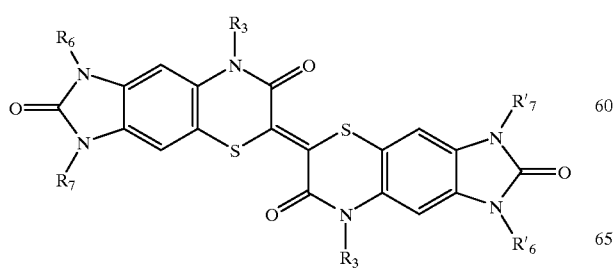

(VIa)

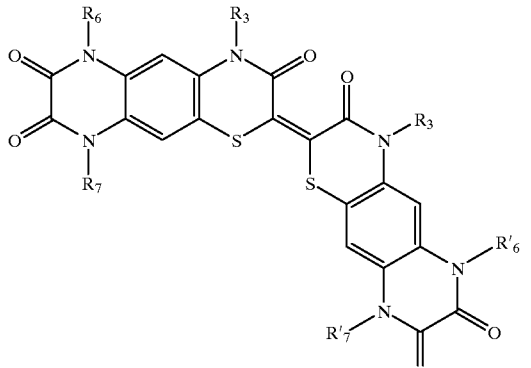

(VIb)

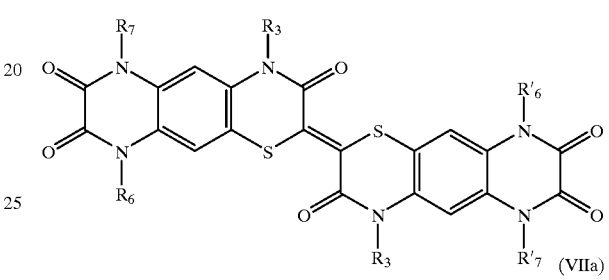

(VIIa)

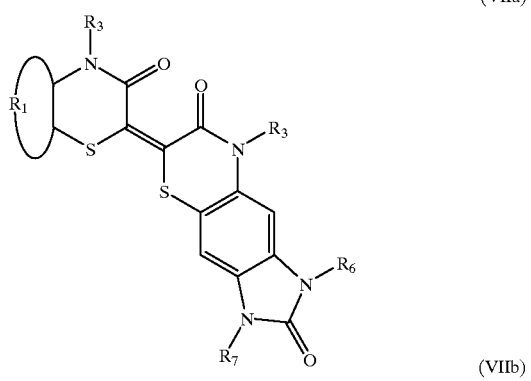

(VIIb)

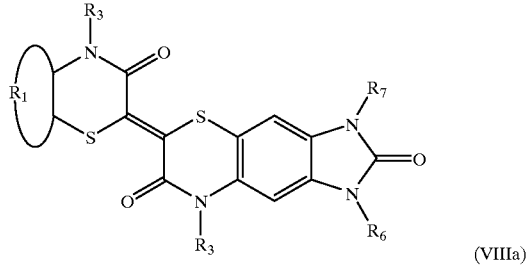

(VIIIa)

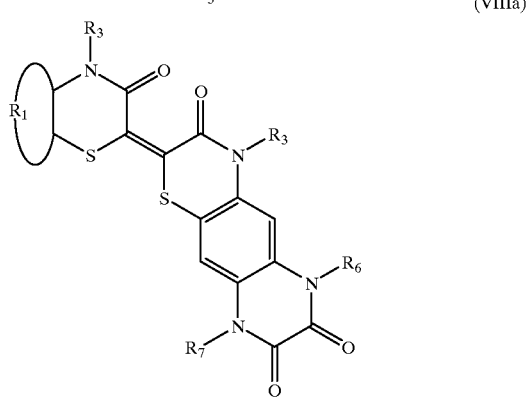

-continued (VIIIb)

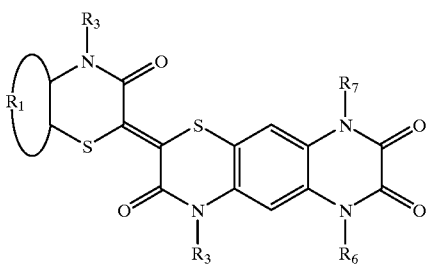

wherein $R_1$ represents the atoms necessary to complete the formation of a substituted or unsubstituted aromatic or alicyclic or heterocyclic ring system, wherein the heterocyclic ring system is a 6-membered N-heteroaromatic ring with one or two N atoms, optionally bearing a fused benzene ring or a benzene ring bearing a fused 5- or 6-membered N-heterocyclic ring with two N atoms; $R_3$ is hydrogen, $C_{1-12}$alkyl or phenyl; $R_6$, $R'_6$, $R_7$ and $R'_7$ are independently an hydrogen, alkyl or aryl group.

9. Cis-thiazine-indigo compounds according to the formula (XI)

(XI)

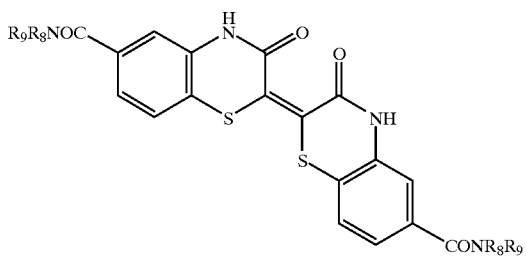

and trans-thiazine-indigo pigments according to the formula (XII)

(XII)

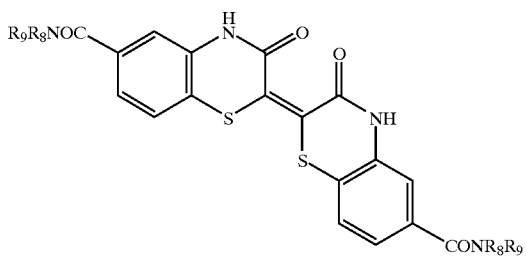

in which formulae $R_8$ and $R_9$ are independently H, $C_{1-8}$alkyl, phenyl, naphthyl, $C_{5-10}$cycloalkyl or

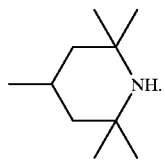

10. A process of forming trans-thiazine-indigo pigments according to formula (XII) of claim 9 by reacting in an inert polar solvent, in the presence or not of an acidic catalyst, a compound of formula (XV) with a compound of formula (IIIa) or (IIIb)

(XV)

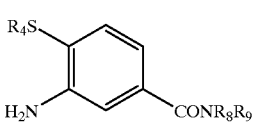

wherein $R_8$ and $R_9$ are independently H, $C_{1-8}$alkyl, phenyl, napthyl, $C_5$–$C_{10}$cycloalkyl or

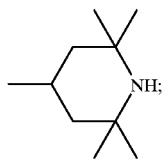

$R_4$ is H or a metallic ion selected from $Na^+$, $K^+$ or $Zn^{2+}$, with the proviso that $R_8=R_9=H$ is excluded;

(IIIa)

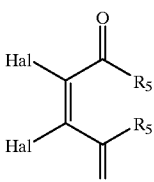

(IIIb)

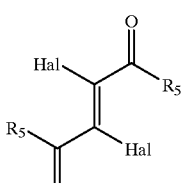

wherein Hal is Cl or Br; and $R_5$ is a leaving group commonly used in substitution reactions at carbonyl carbon atoms.

11. A process of forming cis-thiazine-indigos according to formula (XI) of claim 9 by reduction of a compound of formula (XIII) or (XIV)

(XIII)

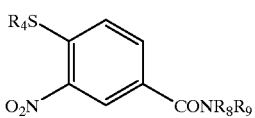

(XIV)

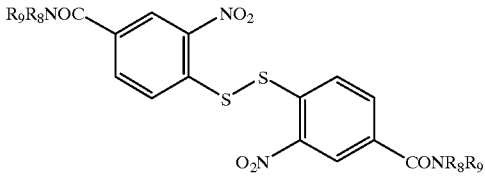

wherein $R_8$ and $R_9$ are independently H, $C_{1-8}$alkyl, phenyl, naphthyl, $C_{5-10}$cycloalkyl or

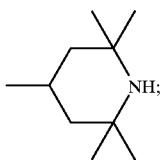

$R_4$ is H or a metallic ion selected from $Na^+$, $K^+$ or $Zn^{2+}$, with the proviso that $R_8=R_9=H$ is excluded, and condensation with a compound of formula (IIIa)

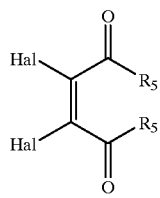

(IIIa)

wherein Hal is Cl or Br; and $R_5$ is a leaving group commonly used in substitution reactions at carbonyl carbon atoms, in an aqueous system comprising water or water and an acidic catalyst or water and a basic catalyst or a mixture of water and a with water miscible solvent, like alcohols, with or without the use of pressure.

12. A process of forming trans-thiazine-indigos according to formula (XII) of claim 9 comprising the steps of reduction of a compound of formulae (XIII) or (XIV)

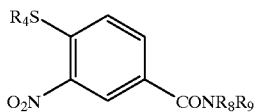

(XIII)

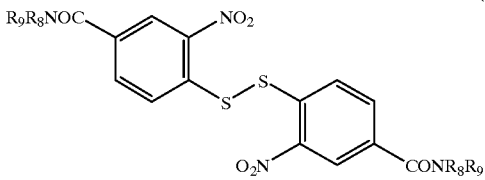

(XIV)

wherein $R_4$ is H or a metallic ion selected from $Na^+$, $K^+$ or $Zn^{2+}$;
$R_8$ and $R_9$ are independently H, $C_{1-18}$alkyl, phenyl, naphthyl, $C_{5-10}$cycloalkyl or

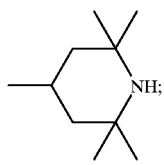

with the proviso that $R_8=R_9=H$ is excluded;
and condensation with a compound of formula (IIIb)

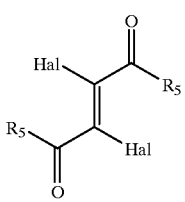

(IIIb)

wherein Hal is Cl or Br; and $R_5$ is a leaving group commonly used in substitution reactions at carbonyl carbon atoms; in the presence of an aqueous system comprising water or water and an acidic catalyst or water and a basic catalyst or a mixture of water and a with water miscible solvent, like alcohols, with or without the use of pressure.

* * * * *